(12) United States Patent
Jin et al.

(10) Patent No.: US 11,382,850 B2
(45) Date of Patent: Jul. 12, 2022

(54) COMPOSITIONS AND METHODS FOR INHIBITING GROWTH OF CARIES-, GINGIVITIS- AND HALITOSIS-CAUSING BACTERIA

(71) Applicant: DoseBiome Inc., Toronto (CA)

(72) Inventors: Ted Jin, Toronto (CA); Mizue Naito, Toronto (CA)

(73) Assignee: DoseBiome Inc., Toronto (CA)

( * ) Notice: Subject to any disclaimer, the term of this patent is extended or adjusted under 35 U.S.C. 154(b) by 0 days.

(21) Appl. No.: 16/299,009

(22) Filed: Mar. 11, 2019

(65) Prior Publication Data

US 2020/0289391 A1    Sep. 17, 2020

(51) Int. Cl.

| | |
|---|---|
| *A61K 8/49* | (2006.01) |
| *A61Q 11/00* | (2006.01) |
| *A61K 8/9789* | (2017.01) |
| *A61K 8/34* | (2006.01) |
| *A61P 1/02* | (2006.01) |
| *A23L 33/105* | (2016.01) |
| *A23L 2/52* | (2006.01) |
| *A61K 8/19* | (2006.01) |

(52) U.S. Cl.
CPC .............. *A61K 8/498* (2013.01); *A23L 2/52* (2013.01); *A23L 33/105* (2016.08); *A61K 8/19* (2013.01); *A61K 8/345* (2013.01); *A61K 8/9789* (2017.08); *A61P 1/02* (2018.01); *A61Q 11/00* (2013.01); *A23V 2002/00* (2013.01)

(58) Field of Classification Search
CPC .......... A61K 8/19; A61K 8/498; A61K 8/345; A61K 8/733; A61K 8/9789; A61K 2800/92; A23L 33/105; A23L 2/52; A23L 33/125; A61P 1/02; A61Q 11/00
See application file for complete search history.

(56) References Cited

U.S. PATENT DOCUMENTS

| | | | | |
|---|---|---|---|---|
| 2006/0188548 | A1* | 8/2006 | Mattson | A23C 9/137 424/439 |
| 2007/0292480 | A1* | 12/2007 | Zhang | A61K 9/0056 424/439 |
| 2008/0026113 | A1* | 1/2008 | Hayashi | A23L 27/30 426/106 |
| 2016/0058053 | A1* | 3/2016 | Markosyan | A23L 2/60 426/548 |

FOREIGN PATENT DOCUMENTS

| | | |
|---|---|---|
| CN | 102670458 | 9/2012 |
| WO | 2001017494 | 3/2001 |
| WO | 2014145602 | 9/2014 |

OTHER PUBLICATIONS

Kuang et al., "Novel Approaches to the Control of Oral Microbial Biofilm," BioMed Research International, vol. 2018, pp. 1-13 (2018).

Nayak et al., "The Effect of Xylitol on Dental Caries and Oral Flora," Clinical, Cosmetic and Investigational Dentistry, vol. 6, pp. 89-94 (2014).

\* cited by examiner

*Primary Examiner* — Lezah Roberts
(74) *Attorney, Agent, or Firm* — Snell & Wilmer L.L.P.

(57) ABSTRACT

The invention provides compositions and methods for topically inhibiting, reducing or preventing growth or biofilm formation of caries-, gingivitis- and/or halitosis-causing bacteria. The composition includes at least about 0.005% (w/v) of tea polyphenols, a pH modulating agent for maintaining a pH of the composition above about 6.5, and at least about 1% (w/v) of a 3-carbon to a 24-carbon sugar alcohol. Also provided are food products or supplements incorporating such compositions.

13 Claims, 15 Drawing Sheets

COMPOSITIONS AND METHODS FOR INHIBITING GROWTH OF CARIES-, GINGIVITIS- AND HALITOSIS-CAUSING BACTERIA

FIELD

This invention relates to compositions and methods for inhibiting growth and/or biofilm formation of caries-, gingivitis- and/or halitosis-causing bacteria. In particular, the invention relates to compositions comprising tea polyphenols, a pH modulating agent and a sugar alcohol for inhibiting growth and/or biofilm formation of caries-, gingivitis- and/or halitosis-causing bacteria.

BACKGROUND

Dental plaque is a biofilm composed of a community of oral microbes that reside on the surface of the tooth. The surface of the teeth is coated by the salivary or acquired enamel pellicle (AEP), consisting mainly of proteins and peptides. While the AEP serves to protect the teeth, the proteins within the AEP can act as binding sites for many oral bacteria. The bacteria, in turn, act as binding sites for other bacteria, leading to the formation of plaque biofilms.

Generally, the plaque microbial community is a normal part of the oral microflora. However, under certain conditions, such as diet or immunocompromised states, the microbial ecology can shift to unfavourable conditions, leading to microbial dysbiosis. In dental caries, excess fermentable carbohydrates (for example, sugar), can lead to the production of organic acids by bacteria such as *Streptococcus mutans*. The bacterial-produced acids cause localized acidification, which can inhibit the growth of many health-associated bacteria, while allowing acidogenic bacteria like *S. mutans* to persist. This increased acidification and decreased microbial diversity creates a feedback loop which promotes further acidification of the local environment. The bacteria-derived acids lead to demineralization of the tooth tissues such as enamel and dentin, which eventually lead to the clinical onset of caries, or tooth decay.

Gingivitis is an inflammatory disease of the gums, which can eventually lead to periodontitis. The main cause is usually dysbiosis of the microbial community in the subgingival space, where the bacteria induce a dysregulated and destructive inflammatory response in the host. Periodontitis can eventually lead to tooth loss, through the continuous inflammation-mediated tissue damage surrounding the teeth, as well as resorption of the supporting alveolar bone. Unlike most diseases caused by dysbiotic microbiota, periodontal diseases are associated with increases in diversity of the microbiome, especially in the gingival crevice. Bacteria associated with periodontal disease include *Porphyromonas gingivalis, Tannerella forsythia, Treponema denticola*, as well as some species of *Fusobacterium* and *Prevotella*. Inflammation is the driving factor for periodontitis-associated bacteria to thrive, as nutrients released through the destruction of gingival tissue promote the growth of the subgingival dysbiotic community. Periodontitis is also linked to systemic health, with increased risk of adverse pregnancy outcomes, rheumatoid arthritis, and atherosclerosis.

Halitosis is the term used to describe unpleasant odour emanating from the breath. 80-90% of halitosis is caused by volatile sulphur compounds (VSCs) produced by oral anaerobic bacteria, commonly residing on the tongue. Halitosis-associated bacteria include *Solobacterium moorei*. Many of the bacteria associated with gingivitis/periodontitis, such as *P. gingivalis, Ta. forsythia*, and *Tr. denticola*, are also VSC producers, and thus, individuals suffering from gingivitis/periodontitis also suffer from halitosis. Treatment of halitosis includes regular tongue cleaning, antiseptics, and professional treatment of pathologic conditions if caused by gingivitis or periodontitis.

Previous efforts toward the correction of dental caries, gingivitis and halitosis have revolved around the use of a toothbrush to remove dental plaque and tongue coatings. Numerous toothpastes and mouth rinses containing various supplements, such as fluoride, are aids in the prevention of dental caries, gingivitis and halitosis. Also in widespread use are electric brushes, floss and adjuncts such as proxy brushes.

However, there remains a need for ingestible compositions for preventing and/or inhibiting the growth and/or biofilm formation of caries-, gingivitis- and halitosis-causing bacteria.

SUMMARY

Various aspects of the present disclosure provide compositions for inhibiting, reducing or preventing growth and/or biofilm formation of caries-, gingivitis- and/or halitosis-causing bacteria, the compositions comprising at least about 0.005% (w/v) of tea polyphenols, a pH modulating agent for maintaining a pH of the compositions above about 6.5, and at least about 1% (w/v) of a sugar alcohol.

Various aspects of the present disclosure also provide a synergistic composition for inhibiting, reducing or preventing growth and/or biofilm formation of caries-, gingivitis- and/or halitosis-causing bacteria, the composition comprising active agents and one or more than one excipient, wherein the active agents consist of at least about 0.005% (w/v) of tea polyphenols, a pH modulating agent for maintaining a pH of the composition above about 6.5, and at least about 1% (w/v) of a sugar alcohol.

The pH of the composition may be between about 6.6 and about 8.5.

The active agents may consist of about 0.005% (w/v) to about 0.1% (w/v) of the tea polyphenols and about 1% (w/v) to about 10% (w/v) of the sugar alcohol and the pH modulating agent for maintaining the pH of the composition between about 6.5 to about 8.5. The sugar alcohol may be a 3-carbon to 24-carbon sugar alcohol.

The tea polyphenols may comprise polyphenols from a liquid tea extract, a powdered tea extract, brewed tea, full leaf tea, synthetic tea polyphenols or a combination thereof.

The tea polyphenols may comprise (+)-catechin (C), (−)-epicatechin (EC), (−)-gallocatechin (GC), (−)-epicatechin gallate (ECG), (−)-epigallocatechin (EGC), (−)-epigallocatechin gallate (EGCG), Kaempferol, quercetin, myricetin, apigenin, luteolin, theaflavin-3-gallate, theaflvin-3-3-digallate or a combination thereof.

The sugar alcohol may be arabitol, erythritol, glycerol, hydrogenated starch hydrolysates, isomalt, lactitol, maltitol, mannitol, sorbitol, xylitol or a combination thereof.

The pH modulating agent may be a food-safe or a food-grade salt. The pH modulating agent may be sodium bicarbonate, potassium carbonate, calcium hydroxide, potassium hydroxide, potassium bicarbonate, sodium hydroxide or a combination thereof.

Also provided are food products comprising such compositions, such as a drink, a concentrate or a syrup, and health supplements comprising such compositions.

Also provided is use of a composition as disclosed herein for inhibiting, reducing or preventing growth and/or biofilm formation of caries-, gingivitis- and/or halitosis-causing bacteria in an oral cavity of a subject.

Also provided is a method of inhibiting, reducing or preventing growth and/or biofilm formation of caries-, gingivitis- and/or halitosis-causing bacteria in an oral cavity of a subject comprising administering a composition as disclosed herein to the subject.

Also provided is a method of inhibiting, reducing or preventing growth or biofilm formation of caries-, gingivitis- and/or halitosis-causing bacteria in an oral cavity of a subject comprising topically contacting a composition as disclosed herein with the oral cavity of the subject.

Also provided is use of a pH modulating agent in combination with a 3-carbon to 24-carbon sugar alcohol for synergistically increasing a topical therapeutic effect of tea polyphenols in inhibiting, reducing or preventing growth and/or biofilm formation of caries-, gingivitis- and/or halitosis-causing bacteria in an oral cavity of a subject.

Also provided is use of a pH modulating agent for synergistically increasing a topical therapeutic effect of tea polyphenols and a 3-carbon to 24-carbon sugar alcohol in inhibiting, reducing or preventing growth and/or biofilm formation of caries-, gingivitis- and/or halitosis-causing bacteria in an oral cavity of a subject.

Other aspects and features of the present invention will become apparent to those of ordinary skill in the art upon review of the following description of specific embodiments of the invention in conjunction with the accompanying claims.

BRIEF DESCRIPTION OF THE DRAWINGS

In drawings which illustrate embodiments of the disclosure,

FIG. 1A shows growth inhibition by tea polyphenols at differing pH; FIG. 1B shows growth inhibition by xylitol at differing pH and FIG. 1C shows combined activity of tea polyphenols and xylitol on growth inhibition at differing pH.

FIG. 2A shows growth inhibition by erythritol at differing pH and FIG. 2B shows combined activity of tea polyphenols and erythritol on growth inhibition at differing pH.

FIG. 3A shows growth inhibition by tea polyphenols at differing pH; FIG. 3B shows growth inhibition by xylitol at differing pH and FIG. 3C shows combined activity of tea polyphenols and xylitol on growth inhibition at differing pH. "ND" in FIG. 3A and FIG. 3C indicates that *S. moorei* could not be detected.

FIG. 6A shows growth inhibition by tea polyphenols at differing pH; FIG. 6B shows growth inhibition by xylitol at differing pH and FIG. 6C shows combined activity of tea polyphenols and xylitol on growth inhibition at differing pH. "ND" in FIG. 6A and FIG. 6C. indicates that *P. gingivalis* could not be detected.

FIG. 7A shows growth inhibition by erythritol at differing pH and FIG. 7B shows combined activity of tea polyphenols and erythritol on growth inhibition at differing pH. "ND" in FIG. 7B indicates that *P. gingivalis* could not be detected.

DETAILED DESCRIPTION

Figure 1A:
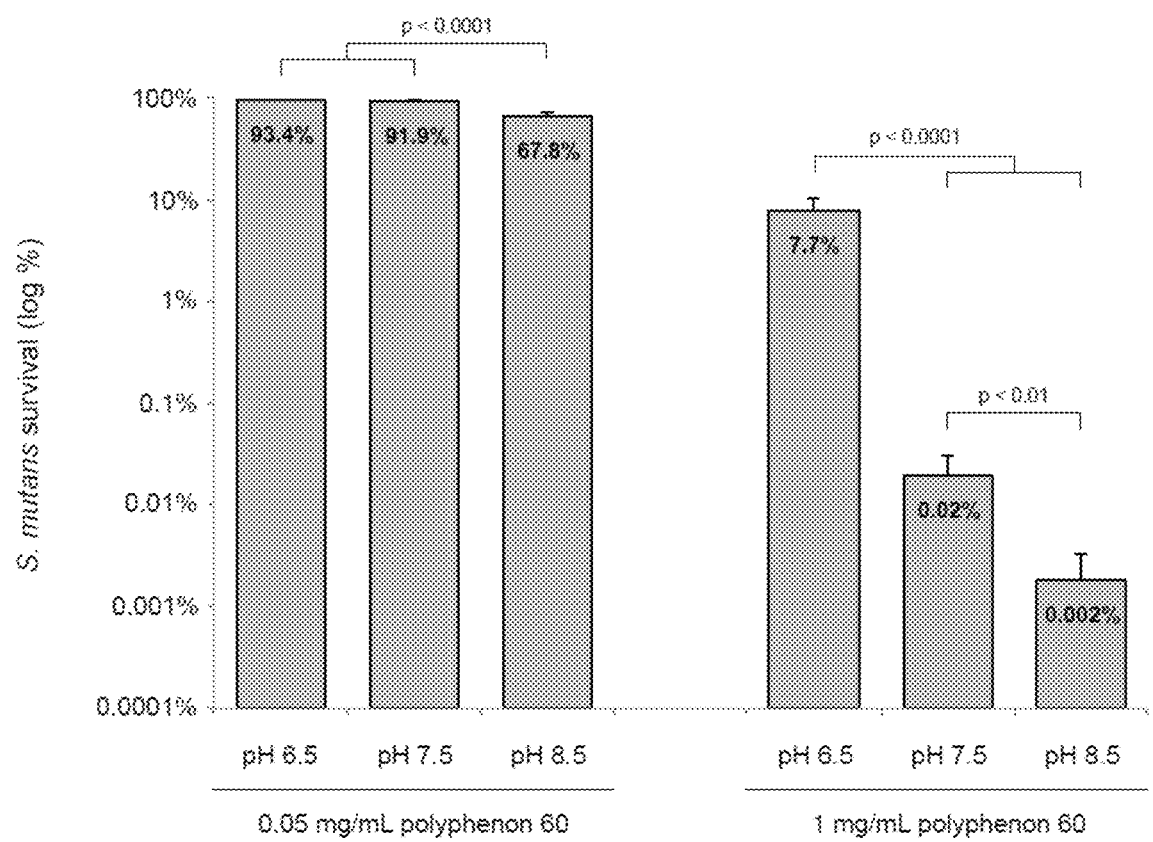
FIG. 1A-FIG. 1C shows inhibitory effect of tea polyphenols and xylitol on *Streptococcus mutans* growth at differing pH.

In the context of the present disclosure, various terms are used in accordance with what is understood to be the ordinary meaning of those terms.

In various embodiments, the disclosure provides compositions for inhibiting, reducing or preventing growth and/or biofilm formation of caries-, gingivitis- and/or halitosis-causing bacteria, the compositions comprising at least about 0.005% (w/v) of tea polyphenols, a pH modulating agent for maintaining a pH of the composition above about 6.5, and at least about 1% (w/v) of a sugar alcohol. The compositions disclosed herein may be used for inhibiting, reducing or preventing growth and/or biofilm formation of caries-, gingivitis- and/or halitosis-causing bacteria in an oral cavity of a subject. The compositions may be for topical contact or application in the oral cavity of the subject.

In various embodiments, the disclosure provides synergistic compositions for inhibiting growth and/or biofilm formation of caries-, gingivitis- and/or halitosis-causing bacteria, the composition comprising active agents and one or more than one excipient, wherein the active agents consist of at least about 0.005% (w/v) of tea polyphenols; a pH modulating agent for maintaining a pH of the composition above about 6.5; and at least about 1% (w/v) of a sugar alcohol. The compositions may be for topical contact in an oral cavity of a subject.

In various embodiments, the disclosure provides synergistically effective topical compositions for topically inhibiting, reducing or preventing growth and/or biofilm formation of caries-, gingivitis- and/or halitosis-causing bacteria in an oral cavity of a subject, the composition comprising active agents, and one or more than one excipient, wherein the active agents consist of about 0.005% (w/v) to about 0.1% (w/v) of tea polyphenols; a pH modulating agent for maintaining a pH of the composition between about 6.5 and about 8.5; and about 1% (w/v) to about 10% (w/v) of a 3-carbon to 24-carbon sugar alcohol.

The terms "topical" and "topically" refer to application of a composition as disclosed herein to a body surface of a subject, such as the teeth or the surfaces of an oral cavity of the subject.

The term "percent weight per volume (w/v)" refers to grams of solute in 100 mL of solution of the composition.

The term "tea polyphenols" refers to polyphenols or polyhydroxyphenols produced by *Camellia sinensis*, whose leaves and leaf buds are used to produce tea. The tea polyphenols may be extracted or derived from *Camellia sinensis* or may be synthetically produced. Tea polyphenols are a mixture of the polyphenolic species extracted from *Camellia sinensis*, components of which include catechins, flaranols, flaraones, chlorogenic acid, phenolic acid, glycosids and their alglycons of plant pigment. Without being bound by any particular theory, it is believed that the catechins are the component of tea polyphenols that provide the physiological efficacious effects of tea. The other components of tea polyphenols may improve the efficacy of the catechins, as well as independently providing efficacious effects.

The term "pH modulating agent" refers to a substance in the composition that acts to change, modify, alter and/or maintain a pH of the composition. In various embodiments, the pH modulating agent is used to maintain the pH of the composition above a minimum value or between certain values.

The term "active agent" refers to a substance which has activity in preventing, reducing or inhibiting growth and/or biofilm formation of caries-, gingivitis- and/or halitosis-causing bacteria. In various embodiments, the active agents of the compositions disclosed herein are the tea polyphenols, the pH modulating agent and the sugar alcohol.

The term "excipient" refers to an inactive substance that serves as a medium for the active agents and may be used in the production of a product comprising the composition to ensure the stability, efficacy, taste and appearance of the product is maintained from the time of production to when the product is consumed by the consumer.

The term "3-carbon to 24-carbon sugar alcohol" refers to organic compounds having the general formula $HOCH_2(CHOH)_nCH_2OH$ where n is 1 to 22.

In various embodiments, the caries-, gingivitis- and/or halitosis-causing bacteria comprise *Streptococcus mutans, Streptococcus sobrinus, Lactobacillus* species, *Porphyromonas gingivalis, Tannerella forsythia, Treponema denticola, Fusobacterium nucleatum, Prevotella intermedia, Prevotella nigrescens, Aggregatibacter actinomycetemcomitans, Solobacterium moorei* or a combination thereof. In various embodiments, the caries-, gingivitis- and/or halitosis-causing bacteria comprise *Streptococcus mutans, Porphyromonas gingivalis, Solobacterium moorei* or a combination thereof.

In various embodiments, the combined effect of the sugar alcohol, pH modulating agent and tea polyphenols on prevention, inhibition and/or reduction of growth and/or biofilm formation of caries-, gingivitis- and/or halitosis-causing bacteria is increased relative to growth and/or biofilm formation of these bacteria in the presence of each component individually.

In various embodiments, growth and/or biofilm formation of caries-, gingivitis- and/or halitosis-causing bacteria is reduced in the presence of a composition comprising the sugar alcohol, the pH modulating agent and tea polyphenols relative to growth and/or biofilm formation of caries-, gingivitis- and/or halitosis-causing bacteria in the presence of the sugar alcohol alone.

In various embodiments, growth and/or biofilm formation of caries-, gingivitis- and/or halitosis-causing bacteria is reduced in the presence of a composition comprising the sugar alcohol, pH modulating agent and tea polyphenols relative to growth and/or biofilm formation of caries-, gingivitis- and/or halitosis-causing bacteria in the presence of the tea polyphenols alone.

In various embodiments, growth and/or biofilm formation of caries-, gingivitis- and/or halitosis-causing bacteria is reduced in the presence of a composition comprising the sugar alcohol and tea polyphenols at higher pH relative to growth and/or biofilm formation of caries-, gingivitis- and/or halitosis-causing bacteria at lower pH. For example, growth and/or biofilm formation of caries-, gingivitis- and/or halitosis-causing bacteria may decrease in the presence of a composition comprising the sugar alcohol and tea polyphenols at pH about 6.5 to about 8.5 relative to growth or biofilm formation of caries-, gingivitis- and/or halitosis-causing bacteria at pH less than about 6.5.

In various embodiments, the tea polyphenols, pH modulating agent and sugar alcohol may act synergistically in reducing, inhibiting or preventing growth and/or biofilm formation of caries-, gingivitis- and/or halitosis-causing bacteria compared to the topical effect of each of these components individually in reducing, inhibiting or preventing growth and/or biofilm formation of caries-, gingivitis- and/or halitosis-causing bacteria in an oral cavity of a subject.

The terms "synergy", "synergistically" and "synergistically effective" refer to the interaction or cooperation of two or more components, substances or other agents to produce a combined effect greater than the sum of their separate effects. Synergy in the context of this disclosure is shown, for example, if performance achieved with a composition comprising a fixed concentration of each component thereof exceeds that of the same concentration of each component on its own. For example, if a composition comprises 1% xylitol, 1 mg/mL tea polyphenols and a pH modulating agent to produce a pH of 7.5, then these components have synergy, are acting synergistically, or are synergistically effective, if the composition inhibits growth of caries-, gingivitis- and/or halitosis-causing bacteria more than 1% xylitol at a pH of about 7.5, 1 mg/mL tea polyphenols at a pH of about 7.5 or the pH modulating agent in an amount sufficient to maintain a pH of about 7.5.

Thus, the pH modulating agent may be used in combination with the sugar alcohol for synergistically increasing a topical therapeutic effect of tea polyphenols in inhibiting, reducing and/or preventing growth and/or biofilm formation of caries-, gingivitis- and/or halitosis-causing bacteria in an oral cavity of a subject. The pH modulating agent may synergistically increase a topical therapeutic effect of tea polyphenols and the sugar alcohol in inhibiting, reducing and/or preventing growth and/or biofilm formation of caries-, gingivitis- and/or halitosis-causing bacteria in the oral cavity of the subject.

The term "therapeutic effect" refers to an effect which reverses a disease state, arrests a disease state, slows the progression of a disease state, ameliorates a disease state, relieves symptoms of a disease state or has any other beneficial consequences for the treated subject. For example, the compositions disclosed herein may have a topical therapeutic effect in inhibiting, reducing and/or preventing growth and/or biofilm formation of caries-, gingivitis- and/or halitosis-causing bacteria. This effect may decrease the likelihood that a subject may develop caries, gingivitis and/or halitosis in the oral cavity or slow the progression of caries, gingivitis and/or halitosis in the oral cavity of the subject.

In various embodiments, the active agents of the compositions disclosed herein consist of at least about 0.005% (w/v) of tea polyphenols, a pH modulating agent in an amount sufficient for the composition to have a pH above about 6.5 and at least about 1% (w/v) of a sugar alcohol. The active agents of the compositions disclosed herein may consist of about 0.005% (w/v) to about 0.1% (w/v) of tea polyphenols, a pH modulating agent in an amount sufficient for the composition to have a pH between about 6.5 and about 8.5, and about 1% (w/v) to about 10% (w/v) of a sugar alcohol. The sugar alcohol may be a 3-carbon to 24-carbon sugar alcohol.

The tea polyphenols may act to decrease the production of bacteria associated with dental caries, gingivitis and/or halitosis. In various embodiments, the compositions disclosed herein comprise between about 0.005% (w/v) and about 0.1% (w/v) of the tea polyphenols or any amount therebetween. For example, the compositions disclosed herein may comprise 0.005% (w/v), 0.006% (w/v), 0.007% (w/v), 0.008% (w/v), 0.009% (w/v), 0.01% (w/v), 0.02% (w/v), 0.03% (w/v), 0.04% (w/v), 0.05% (w/v), 0.06% (w/v), 0.07% (w/v), 0.08% (w/v), 0.09% (w/v) or 0.1% (w/v) of the tea polyphenols. Higher amounts of tea polyphenols should be avoided in the compositions disclosed herein to maintain the palatability of the composition and to avoid any adverse effects of higher concentrations. Furthermore, tea polyphenols are a more costly component of the compositions disclosed herein and thus, minimizing the amount of tea polyphenols in the compositions, while still maintaining the effectiveness of the compositions in inhibiting, reducing or preventing growth and/or biofilm formation of caries-, gingivitis- and/or halitosis-causing bacteria is desired.

In various embodiments, the tea polyphenols may comprise (+)-catechin (C), (−)-epicatechin (EC), (−)-gallocatechin (GC), (−)-epicatechin gallate (ECG), (−)-epigallocatechin (EGC), (−)-epigallocatechin gallate (EGCG), Kaempferol, quercetin, myricetin, apigenin, luteolin, theaflavin-3-gallate, theaflvin-3-3-digallate or a combination thereof. In various embodiments, the tea polyphenols comprise polyphenols from a liquid tea extract, a powdered tea extract, brewed tea (hot or cold), full leaf tea, synthetic tea polyphenols or a combination thereof.

The sugar alcohol may act to reduce the ability of caries-, gingivitis- and/or halitosis-causing bacteria to form biofilms and/or inhibit these bacteria from metabolizing six-carbon dietary sugars into lactic acid. In various embodiments, the sugar alcohol may be a 3-carbon to 24-carbon sugar alcohol. In various embodiments, the sugar alcohol may be arabitol, erythritol, glycerol, hydrogenated starch hydrolysates (HSH), isomalt, lactitol, maltitol, mannitol, sorbitol, xylitol or a combination thereof. For example, the sugar alcohol may be xylitol or erythritol. In various embodiments, the compositions as disclosed herein may comprise at least about 1% (w/v) of the sugar alcohol. For example, the compositions may comprise between about 1% (w/v) and about 10% (w/v) sugar alcohol or any amount therebetween. For example, the compositions may comprise about 1% (w/v), about 2% (w/v), about 3% (w/v), about 4% (w/v), about 5% (w/v), about 6% (w/v), about 7% (w/v), about 8% (w/v), about 9% (w/v) or about 10% (w/v) sugar alcohol. Higher amounts of sugar alcohol in the compositions disclosed herein should be avoided on the basis that these higher amounts may be excessively sweet and/or may have adverse consequences for consumers, such as, for example, diarrhea. Furthermore, sugar alcohol is a more costly component of the compositions disclosed herein and thus, minimizing the amount of sugar alcohol in the compositions, while still maintaining the effectiveness of the compositions in inhibiting, reducing or preventing growth and/or biofilm formation of caries-, gingivitis- and/or halitosis-causing bacteria is desired.

The pH modulating agent is present in the composition in an amount sufficient for the composition to have a pH above about 6.5. For example, the pH of the composition may be between about 6.5 and about 8.5 or any value therebetween. In various embodiments, the pH of the composition may be about 6.5, about 6.6, about 6.7, about 6.8, about 6.9, about, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4 or about 8.5.

The pH modulating agent may be a food-safe salt or a food-grade salt. The terms "food-safe" and "food-grade" refer to salts suitable for ingestion by a subject without undue toxicity, incompatibility, instability, irritation, allergic response and the like. For example, the pH modulating agent may comprise sodium bicarbonate, potassium bicarbonate, calcium hydroxide, potassium hydroxide, potassium bicarbonate, sodium hydroxide or a combination thereof.

In various embodiments, the composition comprises one or more than one excipient. The one or more than one excipient is a non-active agent in the composition and does not have any activity in preventing, reducing and/or inhibiting growth and/or biofilm formation of caries-, gingivitis- and/or halitosis-causing bacteria. The one or more than one excipient may be water, a binder, a lubricant, a disintegrant, a thickener, a dispersing agent, a suspending agent, an absorbent, a preservative, an anti-microbial agent, a surfactant, a colorant, a viscosity modifier, a plasticizing agent, a foaming agent, water, glycerin, a flavouring agent, an emulsifier, polyglycitol syrup or any combination thereof. The one or more than one excipient and amount thereof may be chosen to modify the taste, viscosity and/or texture of the composition. For example, sodium alginate is a thickener that may be added to the composition to increase the its viscosity.

In various embodiments, the compositions of the present disclosure may be prepared as a drink, a supplement, a food product, a mouthwash, a personal care product, a functional food, a cosmetic, a cream, a dentifrice, a varnish, a gel, a confectionary, a chewing gum, a syrup, a concentrate, a suspension, a tablet, a capsule, a paste, a mouth spray, a topical oral gel, a lozenge or a powder, with the one or more than one excipient. In various embodiments, the composition is a powder. In various embodiments, the composition is a drink. The drink may comprise between about 79% (v/v) and about 99% (v/v) water and other excipients to achieve a certain flavour for the drink. In various embodiments, the food product is a concentrate or syrup. The concentrate or syrup may comprise between about 30% (v/v) and about 35% (v/v) water. In various embodiments, the composition is prepared as a health supplement with the one or more than one excipient.

In various embodiments, the compositions disclosed herein are for topical use by topically inhibiting, reducing and/or preventing growth or biofilm formation of caries-, gingivitis- and/or halitosis-causing bacteria in an oral cavity of a subject. The subject may be an animal, such as a mammal and more particularly, a human. The topical effects of the compositions disclosed herein occur when the composition contacts or is applied to the oral cavity of the subject, such as the teeth or other surfaces of the oral cavity. This contact occurs when the composition enters the oral cavity. For example, the compositions disclosed herein may be for consumption or ingestion by a subject or may be used as a rinse that is not consumed by the subject. In either case, the composition contacts the oral cavity and provides the therapeutic effect.

EXAMPLES

These examples illustrate various aspects of the invention, evidencing a variety of conditions for preparing compositions for inhibiting, reducing or preventing growth and/or biofilm formation of caries-, gingivitis- and/or halitosis-causing bacteria.

As used herein, the term "about" refers to an approximately +/−10% variation from a given value. It is to be understood that such a variation is always included in any given value provided herein, whether or not it is specifically referred to.

Methods and Materials

Bacterial Strains and Culture Conditions

*Solobacterium moorei* DSM 22971 and *Porphyromonas gingivalis* ATCC 33277 were grown in Schaedler's broth (Himedia) or Brucella blood agar with hemin and vitamin K (Hardy Diagnostics) under anaerobic conditions at 37° C. Anaerobic conditions were maintained using the Anaerogen atmosphere generation system (Oxoid). *Streptococcus mutans* UA159 were grown in Brain Heart Infusion (BHI; Hardy Diagnostics) under 5% $CO_2$ at 37° C.

Test Products

Various concentrations of xylitol (Acros Organics), erythritol (Acros Organics) and/or polyphenon 60 (Sigma) were dissolved in Schaedler's broth or BHI broth. Polyphenon 60 is a green tea extract containing a mixture of polyphenolic compounds, with a minimum 60% of total catechins. The mixtures were pH adjusted using either hydrochloric acid or sodium hydroxide to a final pH of 6.5±0.1, 7.5±0.1 or 8.5±0.1. All test products were filter-sterilized after pH adjustment.

Growth Inhibition Assay

Using 96-well plates, *S. moorei* or *P. gingivalis* were grown in Schaedler's broth containing various amounts of xylitol, erythritol and/or polyphenon 60 at an initial $OD_{595}$ of 0.01 at 37° C. under anaerobic conditions. After 48 h of incubation, various dilutions of the cells were spotted into Brucella blood agar with hem in and vitamin K, and incubated for 48 h for *S. moorei*, and for 72 h for *P. gingivalis*. Cell counts were normalized against growth in Schaedler's broth adjusted to their respective testing pH.

For *S. mutans*, the above experiment was performed using BHI broth, at an initial $0D_{595}$ of 0.005. After cells were incubated in their test products for 20 h at 37° C. under 5% $CO_2$, various dilutions were spotted onto BHI agar and incubated for a further 48 h at 5% $CO_2$ to allow for colony counting. Cell counts were normalized against growth in BHI adjusted to their respective testing pH.

Example 1: Inhibitory Effect of Tea Polyphenols and Xylitol on *Streptococcus mutans* Growth at Differing pH

*S. mutans* UA159 was grown in the presence of 1% or 10% (w/v) xylitol or 0.05 mg/mL (0.005% (w/v)) or 1 mg/mL (0.1% (w/v)) tea polyphenols (polyphenol 60) in acidic (6.5±0.1), neutral (7.5±0.1) or alkaline (8.5±0.1) pH. The percent inhibition was measured by normalizing the results against *S. mutans* grown in media with the corresponding pH adjustment. As shown in FIG. 1A, tea polyphenols alone at a concentration of 0.05 mg/mL showed little inhibitory activity on growth of *S. mutans* at pH 6.5, but the inhibitory activity increased with increasing pH. FIG. 1A also shows that a composition of 1 mg/mL polyphenon 60 similarly shows stronger activity against growth of *S. mutans* at higher pH.

Figure 1B:
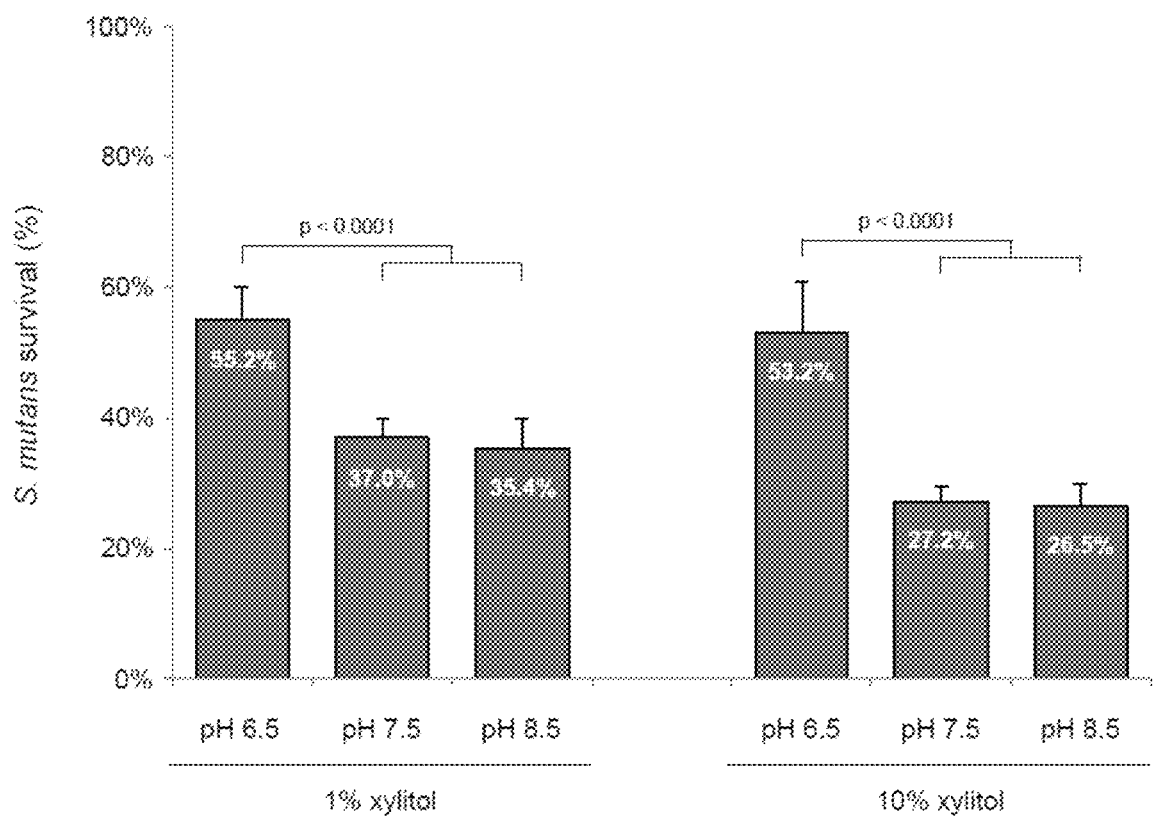

FIG. 1B shows the effect of 1% (w/v) or 10% (w/v) xylitol in acidic (6.5±0.1), neutral (7.5±0.1) or alkaline (8.5±0.1) pH on growth of *S. mutans*. Both of these concentrations of xylitol had inhibitory activity on growth of *S. mutans*, with their inhibitory activity increasing with increasing pH.

Figure 1C:
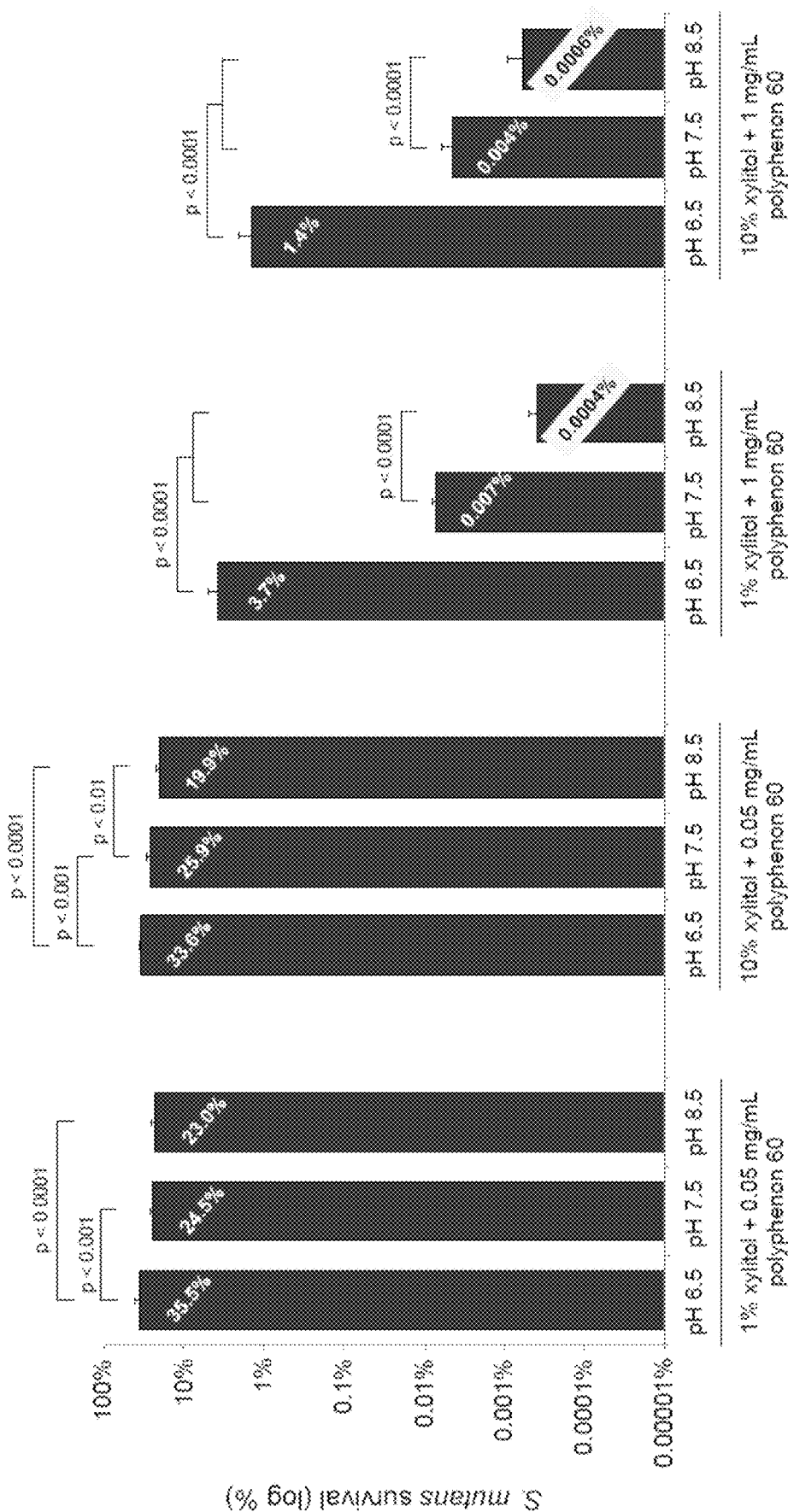

The survival of *S. mutans* in the presence of a composition comprising xylitol and polyphenol 60, with the effect of increasing pH, is shown in FIG. 1C. With a lower pH, the inhibitory activity decreases, while at higher pH, the inhibitory activity is increased. The combination of xylitol and polyphenon 60 resulted in decreased survival of *S. mutans* when compared to the inhibitory activity of either xylitol or polyphenon 60 alone. The combined activity of xylitol and polyphenon 60 showed decreasing survival with more alkaline pH. A composition of 1% xylitol and 1 mg/mL polyphenon 60 at pH 8.5 showed the lowest survival of *S. mutans* (0.0004%) with a similar survival of *S. mutans* being shown with 10% xylitol and 1 mg/mL polyphenon 60 at pH 8.5 (0.0006%).

Example 2: Inhibitory Effect of Tea Polyphenols and Erythritol on *Streptococcus mutans* Growth at Differing pH

Figure 2A:
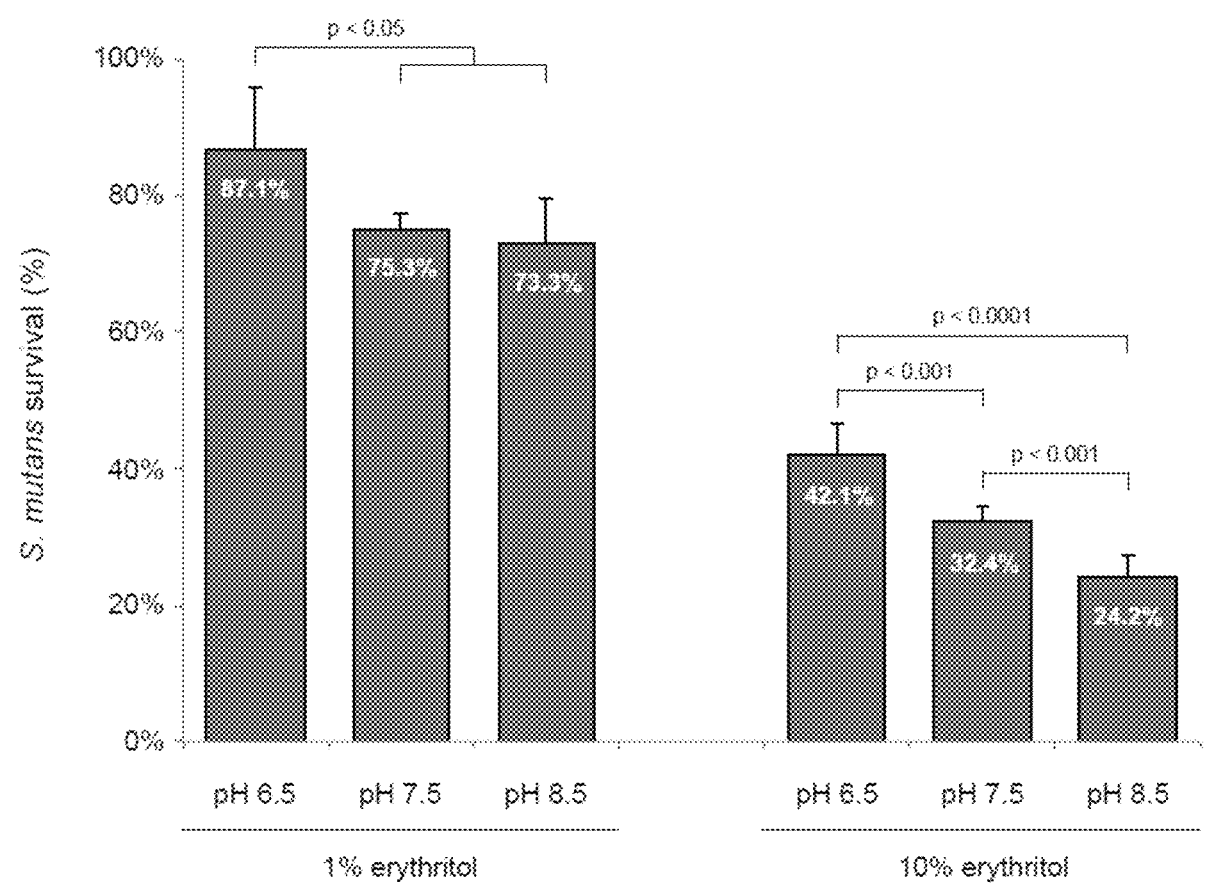
FIGS. 2A and 2B shows inhibitory effect of tea polyphenols and erythritol on *Streptococcus mutans* growth at differing pH.

*S. mutans* UA159 was grown in the presence of 1% (w/v) or 10% (w/v) erythritol or 0.05 mg/mL (0.005% (w/v)) or 1 mg/mL (0.1% (w/v)) tea polyphenols (polyphenon 60; FIG. 1A) in acidic (6.5±0.1), neutral (7.5±0.1) or alkaline (8.5±0.1) pH. The percent inhibition was measured by normalizing the results against *S. mutans* grown in media with the corresponding pH adjustment. As shown in FIG. 2A, 1% (w/v) or 10% (w/v) erythritol compositions inhibit growth of *S. mutans* with inhibition increasing with more alkaline pH. A composition of 10% (w/v) erythritol exhibited greater inhibition at all pH values compated to 1% (w/v) erythritol.

Figure 2B:
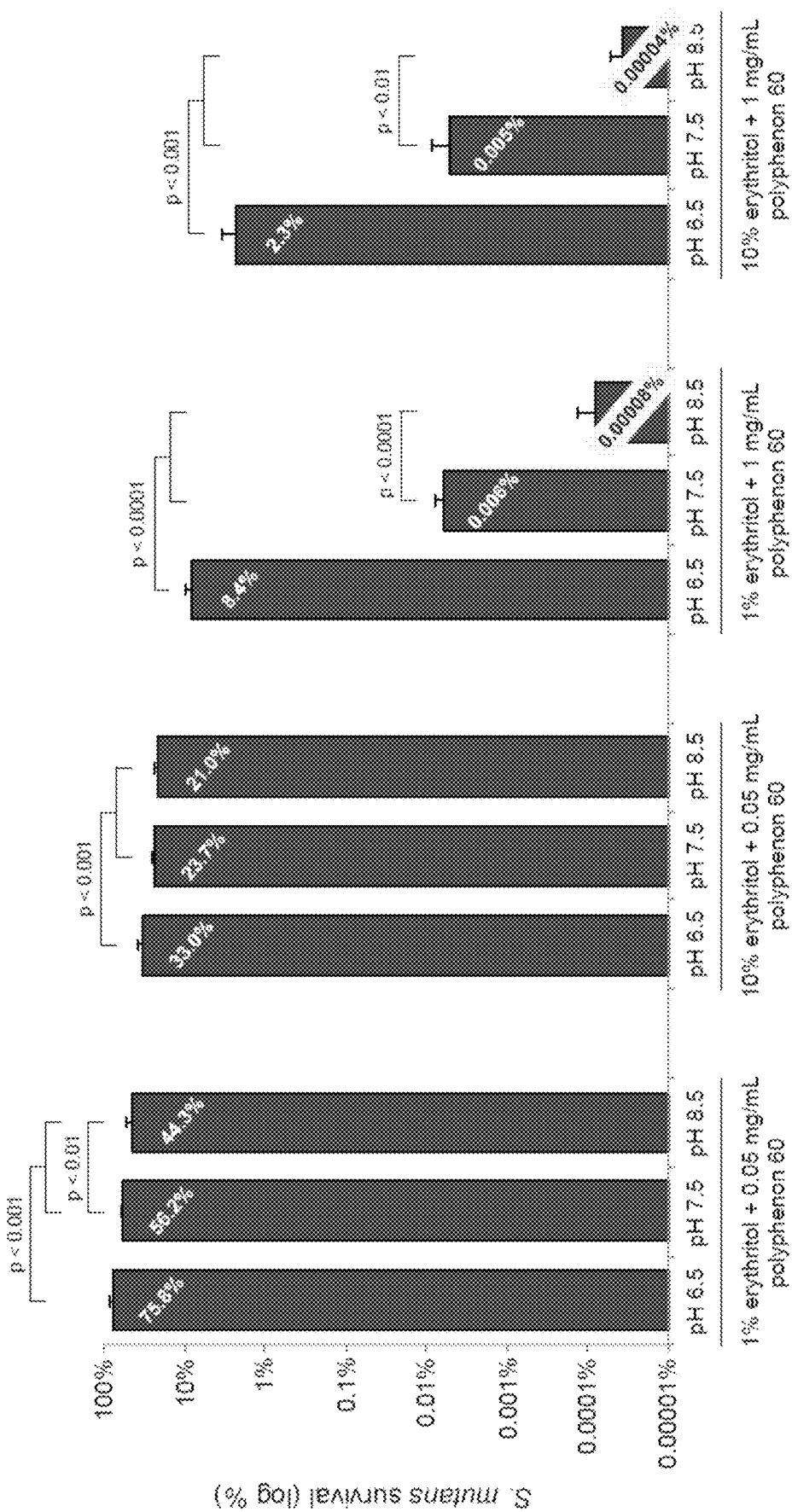

The survival of *S. mutans* in the presence of a composition comprising erythritol and polyphenol 60 at various pH is shown in FIG. 2B. With a lower pH, the inhibitory activity decreases, while at higher pH, the inhibitory activity is increased. The combination of 1% erythritol and 1 mg/mL polyphenon 60 at pH 8.5 resulted in a *S. mutans* surivival of 0.00008% and the combination of 10% erythritol and 1 mg/mL polyphenon 60 resulted in a *S. mutans* survival of 0.00004%, which is an increased inhibitory effect on *S. mutans* survival compared to erythritol or polyphenon 60 alone at the same pH. The same results were obtained for pH 6.5 and 7.5. For all compositions, increasing the pH above 6.5 showed greater inhibitory activity.

Example 3: Inhibitory Effect of Tea Polyphenols and Xylitol on *Solobacterium moorei* Growth at Differing pH

*S. moorei* DSM 22971 was grown in the presence of 1% (w/v) or 10% (w/v) xylitol or 0.05 mg/mL, 0.1 mg/mL, 0.2 mg/mL or 1 mg/mL tea polyphenols (polyphenon 60) in acidic (pH 6.5±0.1), neutral (7.5±0.1) or alkaline (pH 8.5±0.1) pH. The percent inhibition was measured by normalizing the results against *S. moorei* grown in media with the corresponding pH adjustment.

Figure 3A:
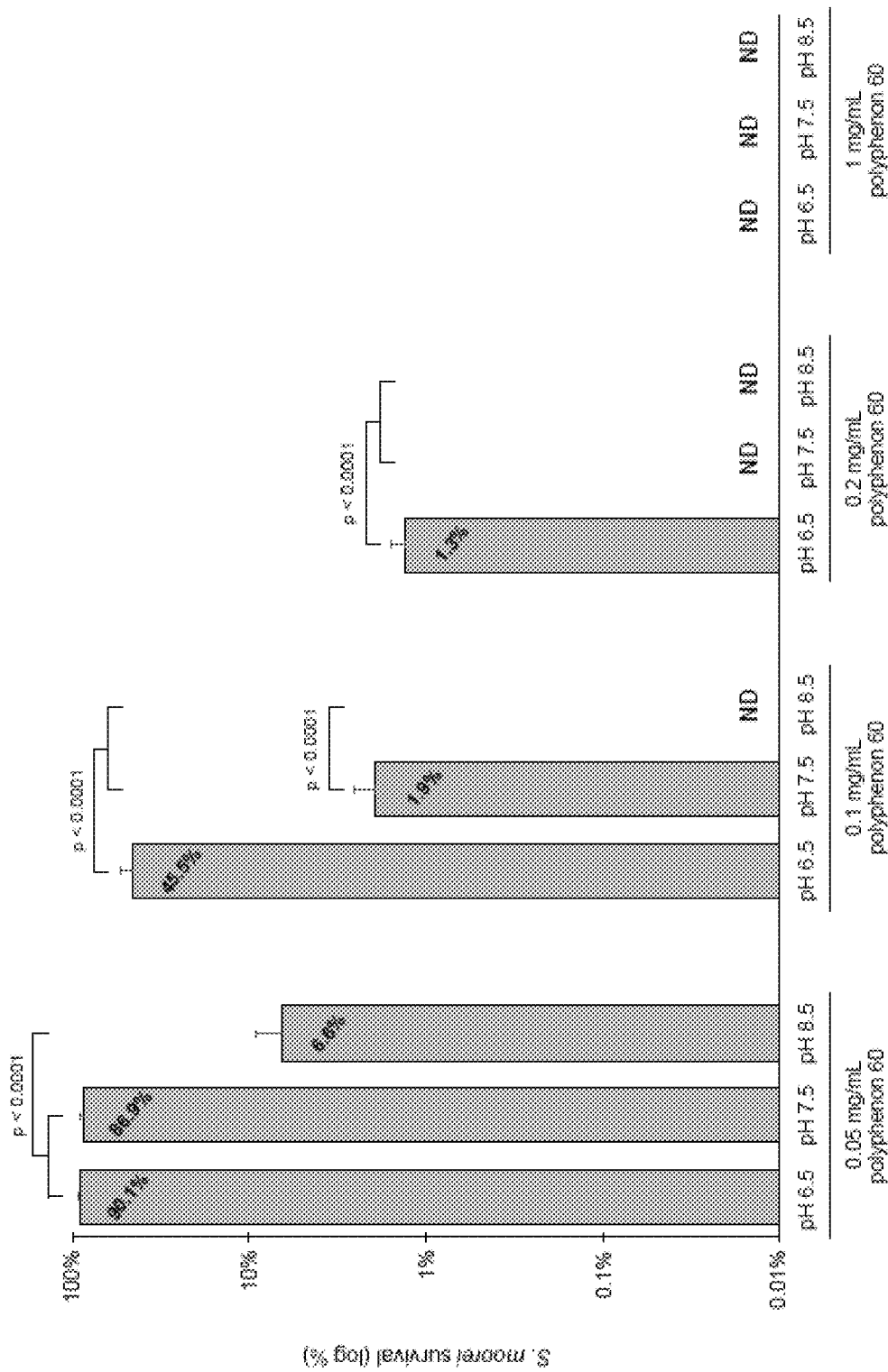
FIG. 3A-3C shows inhibitory effect of tea polyphenols and xylitol on *Solobacterium moorei* growth at differing pH.

As shown in FIG. 3A, the inhibitory effect of tea polyphenols alone on growth of *S. moorei* was dependent on pH. At 1 mg/mL polyphenon 60, all pH conditions kill *S. moorei* beyond detection (ND=not detectable). At 0.2 mg/mL polyphenon 60, pH conditions of 7.5 or 8.5 kill *S. moorei* beyond detection and *S. moorei* survival was 1.3% at pH 6.5.

Figure 3B:
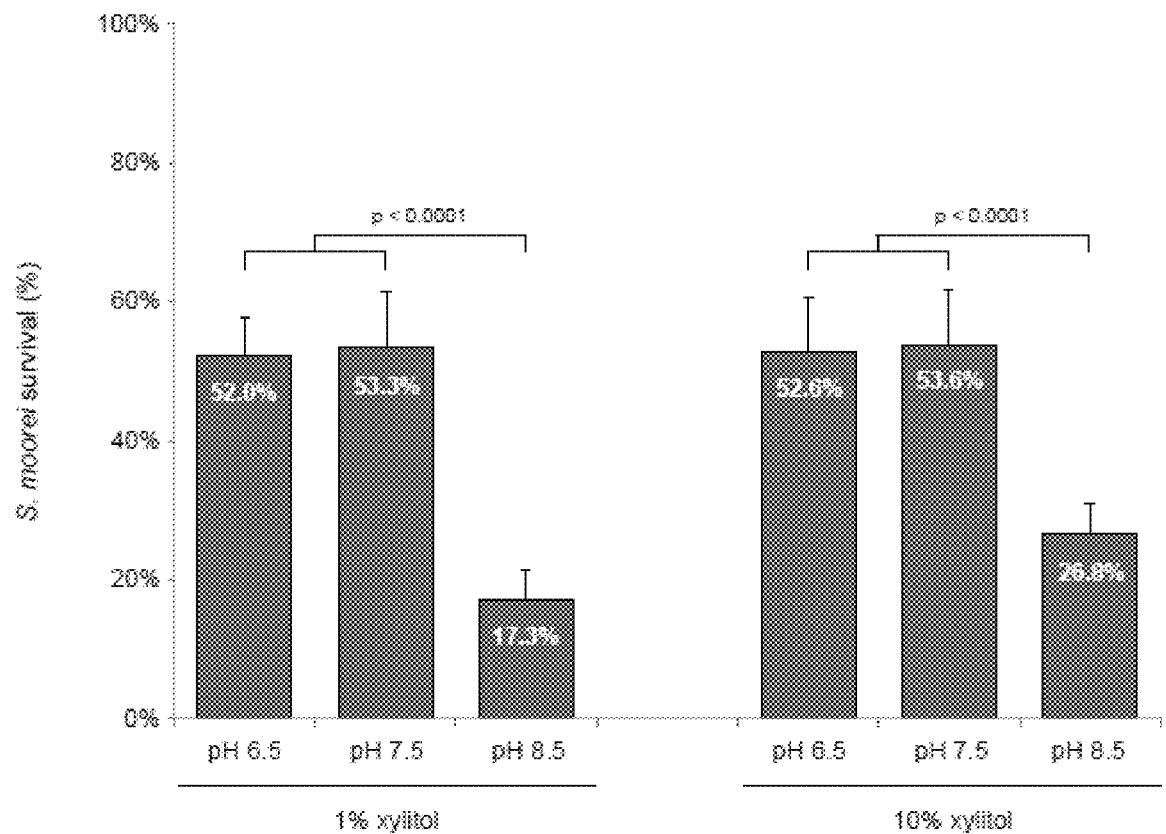

FIG. 3B shows the effect of 1% (w/v) or 10% (w/v) xylitol in acidic (pH 6.5±0.1), neutral (7.5±0.1) or alkaline (pH 8.5±0.1) pH on growth of *S. moorei*. Both of these concentrations of xylitol had similar inhibitory activity on growth of *S. moorei* at pH 6.5 and 7.5 (52.0% survival for 1% xylitol and 52.6% survival for 10% xylitol at pH 6.5, and 53.3% survival for 1% xylitol and 53.6% survival for 10% xylitol at pH 7.5). Survival of *S. moorei* in 1% xylitol at pH 8.5 was 17.3% compared to 26.8% survival in 10% xylitol at the same pH.

Figure 3C:
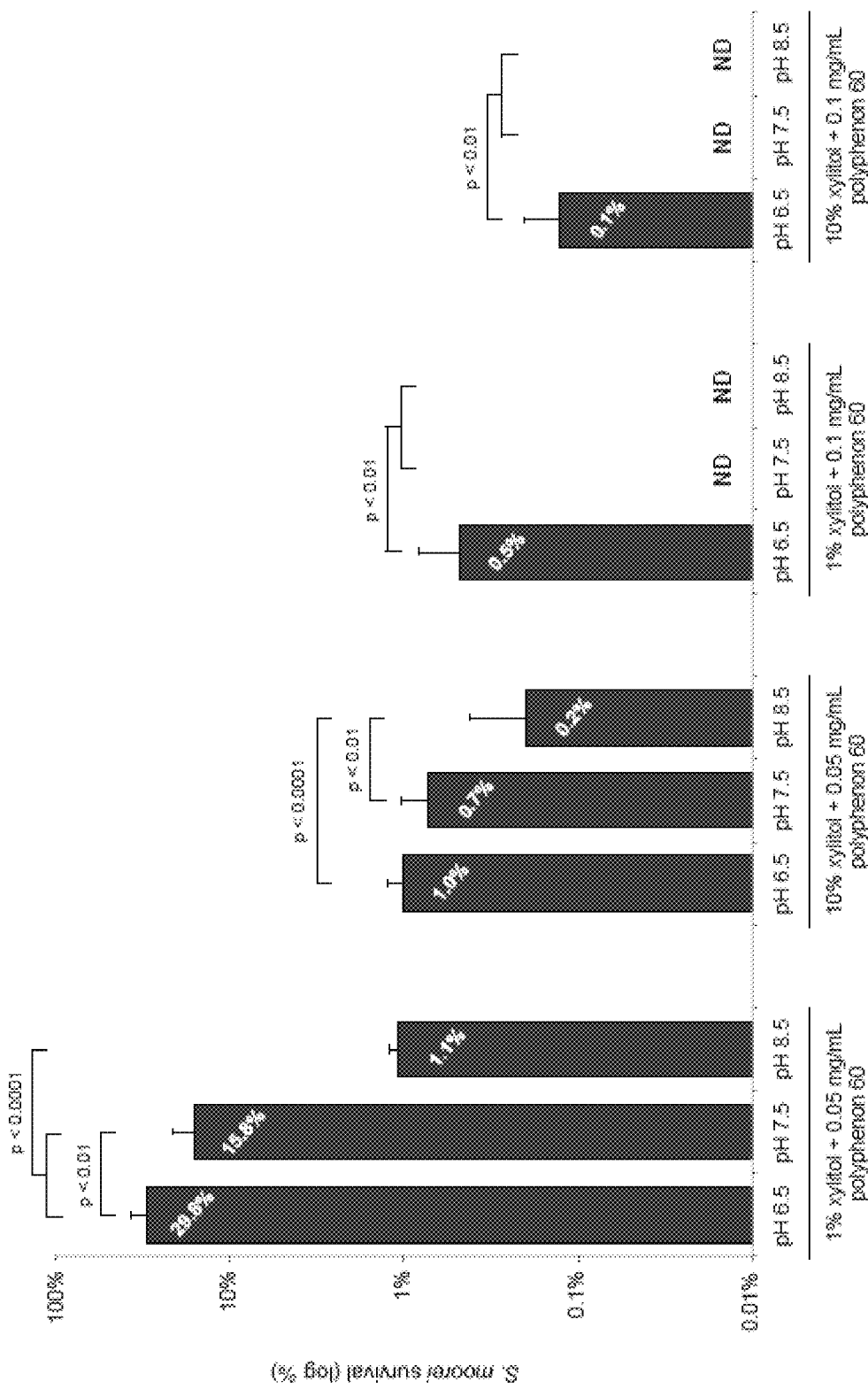

The survival of *S. moorei* in the presence of a composition comprising xylitol, pH modulating agent and tea polyphenols (polyphenon 60) is shown in FIG. 3C. The combination of sugar alcohol and tea polyphenols resulted in increased inhibition of growth of *S. moorei* compared to either xylitol or polyphenon 60 alone, at the same pH. Furthermore, the effect of the combination of xylitol and polyphenon 60 increased with increasing pH. For example, a composition comprising 1% xylitol and 0.05 mg/mL polyphenon 60 resulted in 29.8% *S. moorei* survival at pH 6.5, 15.8% *S. moorei* survival at pH 7.5 and 1.1% *S. moorei* survival at pH 8.5.

Example 4: Effect of Erythritol on *Solobacterium moorei* Growth at Differing pH

Figure 4:
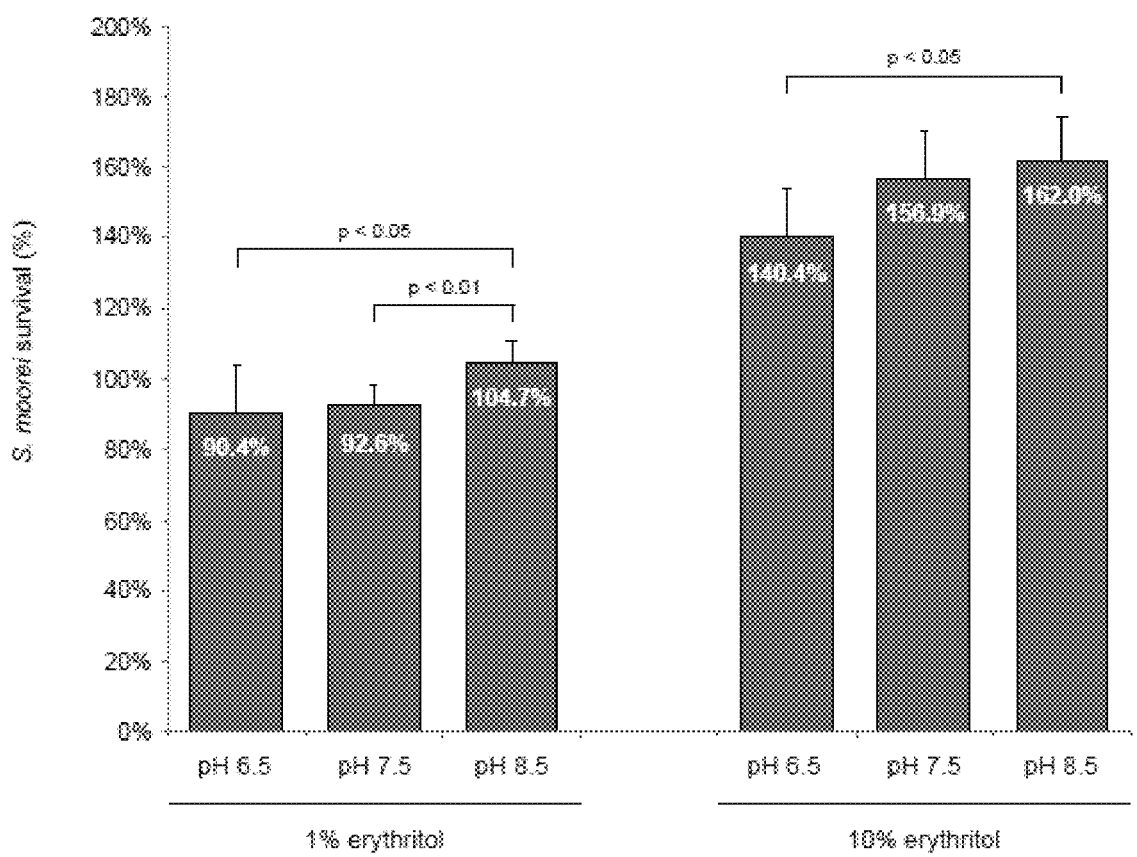
FIG. 4 shows the effect of erythritol on *Solobacterium moorei* growth at differing pH.

*S. moorei* DSM 22971 was grown in the presence of erythritol in acidic (pH 6.5±0.1), neutral (7.5±0.1) or alkaline (pH 8.5±0.1) pH. The percent survival was measured by normalizing the results against *S. moorei* grown in media with the corresponding pH adjustment. As shown in FIG. 4, increasing the concentration of erythritol from 1% (w/v) to 10% (w/v) resulted in increased survival of *S. moorei* at each pH tested. The survival of *S. moorei* also increased with increasing pH, for example, *S. moorei* survival in 10% erythritol was 140.4% at pH 6.5, 156.9% at pH 7.5 and 162.0% at pH 8.5. Without being bound by any particular theory, the erythritol may be used as a carbon source by *S. moorei*, and its supplementation is able to further promote the growth of *S. moorei* compared to media alone.

Example 5: Inhibitory Effect of Tea Polyphenols and Erythritol on *Solobacterium moorei* Growth at Differing pH

Figure 5:
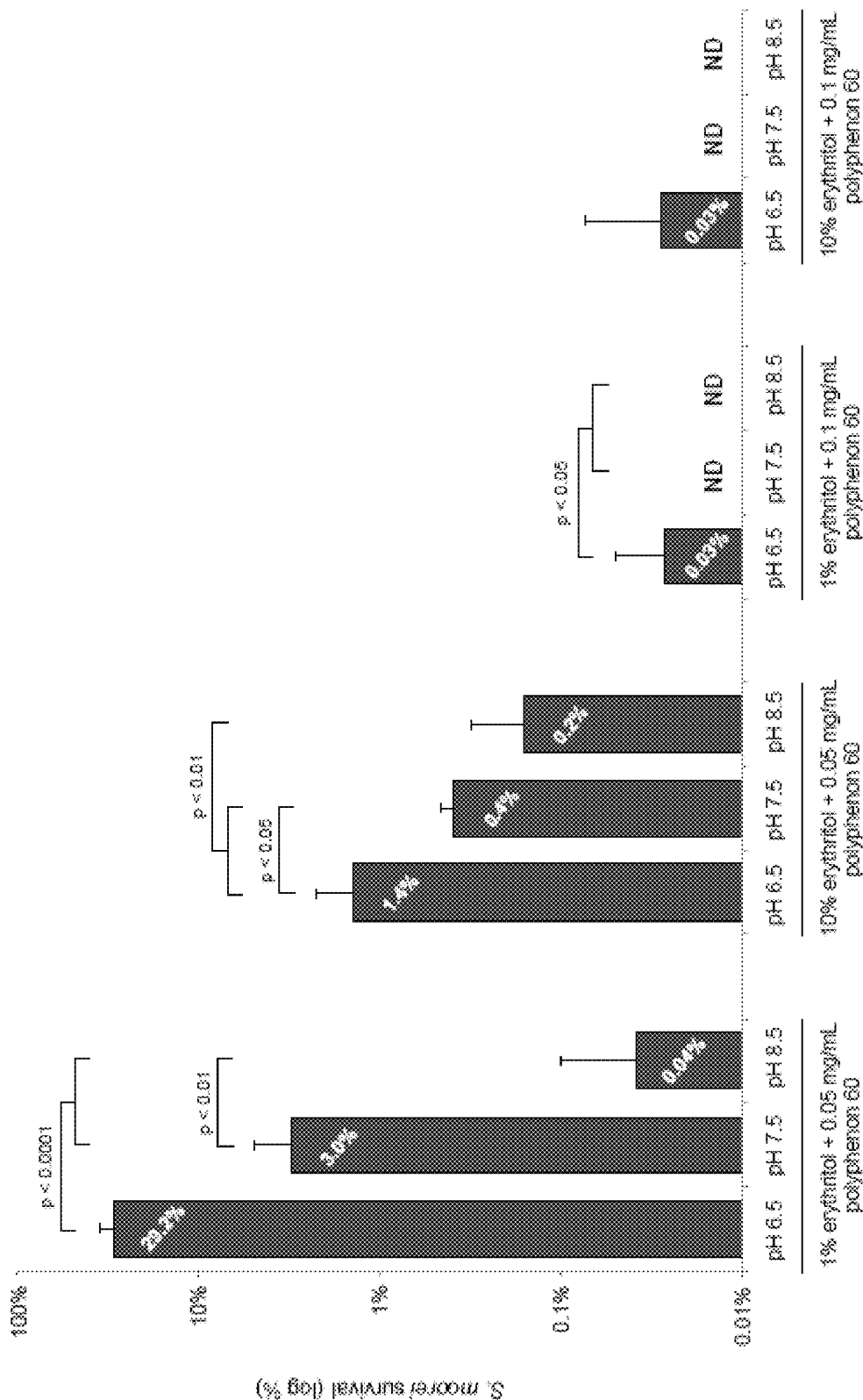
FIG. 5 shows inhibitory effect of tea polyphenols and erythritol on *Solobacterium moorei* growth at differing pH. "ND" in FIG. 5 indicates that *S. moorei* could not be detected.

*S. moorei* DSM 22971 was grown in the presence of erythritol and tea polyphenols (polyphenon 60) in acidic (pH 6.5±0.1), neutral (7.5±0.1) or alkaline (pH 8.5±0.1) pH. The percent inhibition was measured by normalizing the results against *S. moorei* grown in media with the corresponding pH adjustment. An upper limit of 0.1 mg/mL polyphenon 60 was used in order to be able to assess the pH effects. FIG. 5 shows that the combination of erythritol and polyphenon 60 results in reduced survival of *S. moorei*, and this effect is enhanced with increasing pH (ND=not detected). For example, the survival of *S. moorei* in a combination of 1% erythritol and 0.05 mg/mL polyphenon 60 was 29.2% at pH 6.5, 3.0% at pH 7.5 and 0.04% at pH 8.5. This result was observed despite the trend shown in FIG. 4 where erythritol on its own at varying concentrations did not inhibit *S. moorei* growth at any pH.

Example 6: Inhibitory Effect of Tea Polyphenols and Xylitol on *Porphyromonas gingivalis* Growth at Differing pH

Figure 6A:
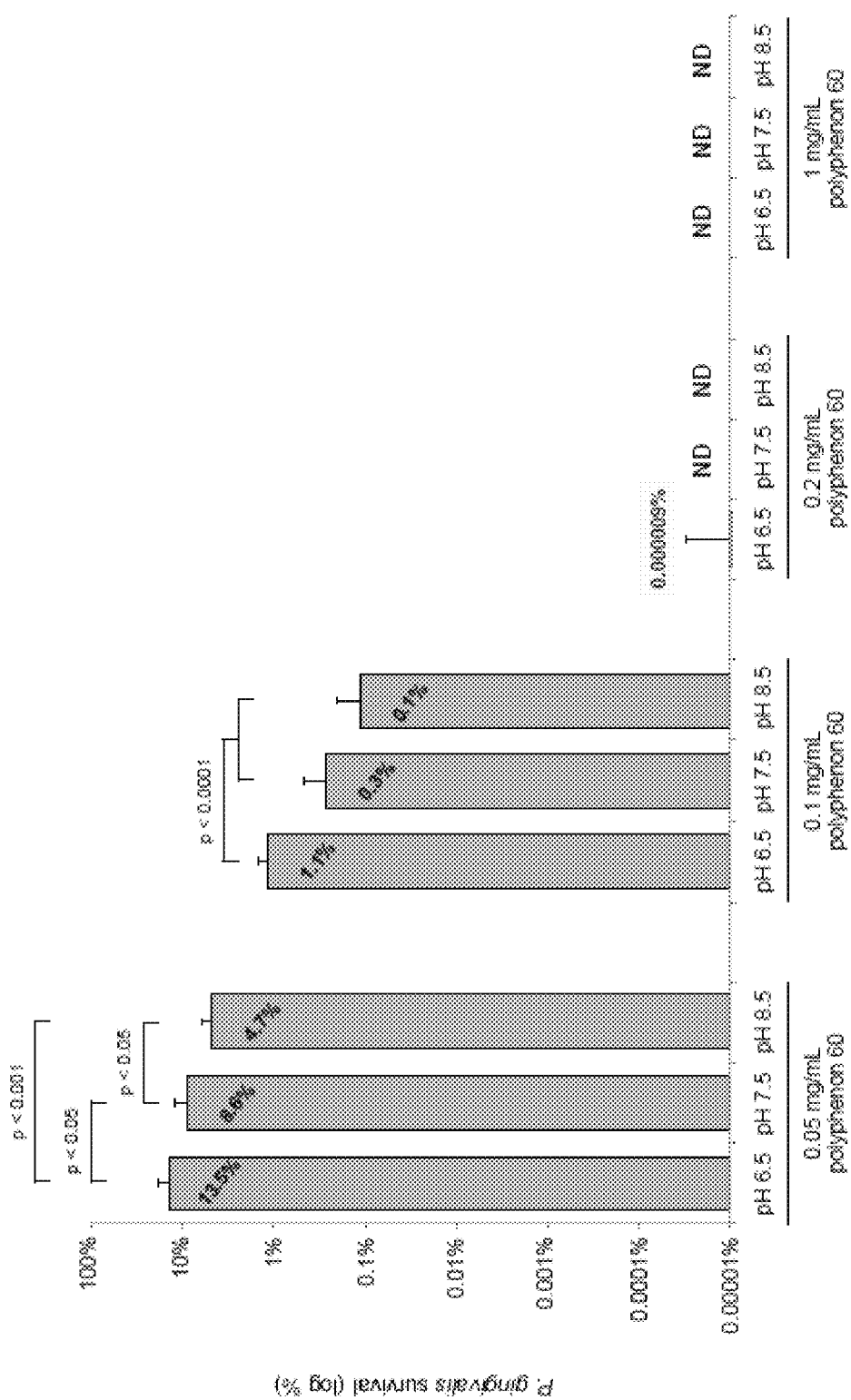
FIG. 6A-6C shows inhibitory effect of tea polyphenols and xylitol on *Porphyromonas gingivalis* growth at differing pH.

*P. gingivalis* ATCC 33277 was grown in the presence of xylitol and tea polyphenols (polyphenon 60) in acidic (pH 6.5±0.1), neutral (7.5±0.1) or alkaline (pH 8.5±0.1) pH. The percent inhibition was measured by normalizing the results against *P. gingivalis* grown in media with the corresponding pH adjustment. FIG. 6A shows growth inhibition of polyphenon 60 at differing pH, where increased pH enhances the inhibitory activity of the polyphenols. At concentrations greater than 0.2 mg/mL polyphenon 60, all pH conditions kill *P. gingivalis* beyond detection.

Figure 6B:
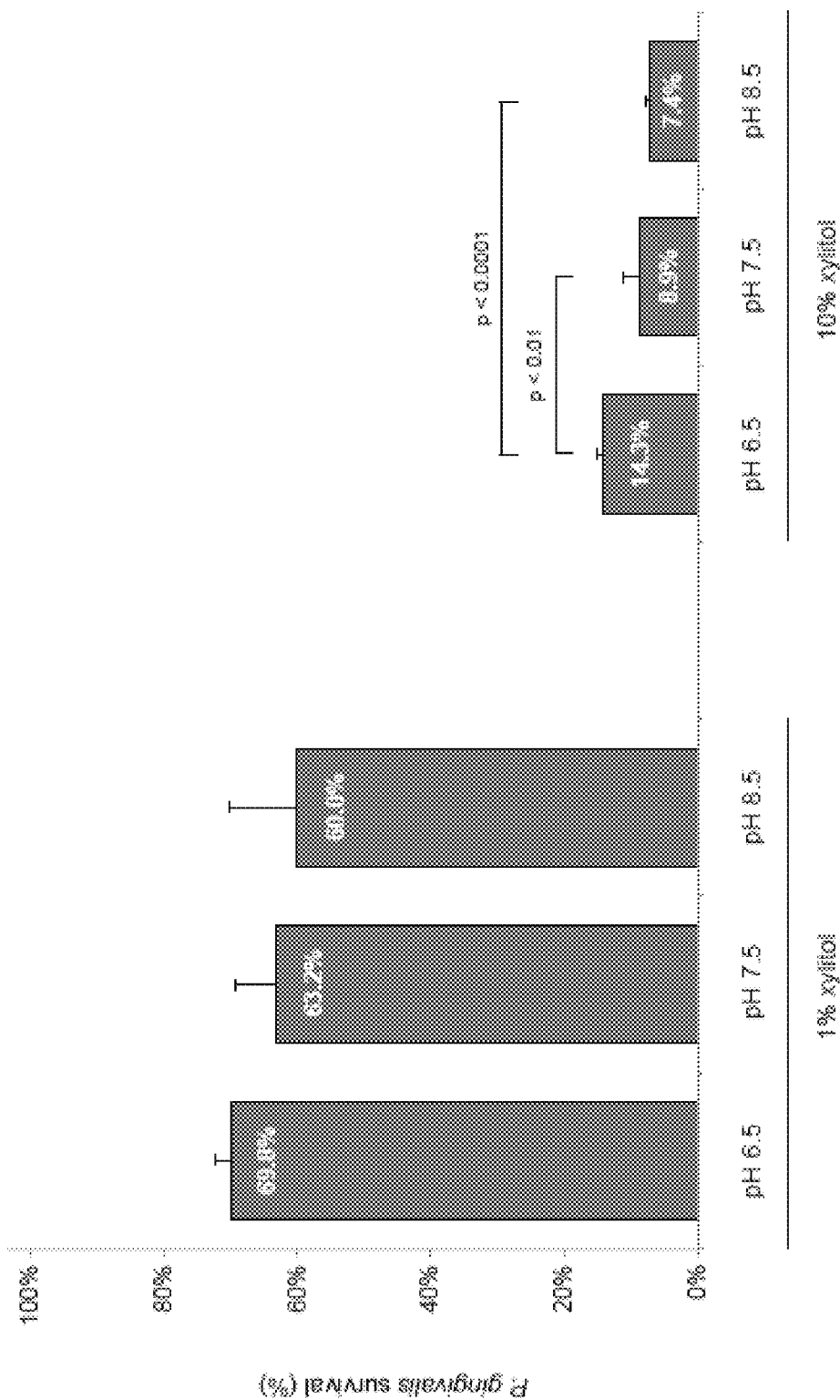

FIG. 6B shows *P. gingivalis* survival in the presence of 1% (w/v) or 10% (w/v) xylitol at various pH. The results show a decrease in survival with increasing pH, although the effect on survival of *P. gingivalis* is greater for 10% xylitol compared to 1% xylitol. Survival of *P. gingivalis* in 1% (w/v) xylitol was 69.8% at pH 6.5, 63.2% at pH 7.5 and 60.0% at pH 8.5. Survival of *P. gingivalis* in 10% xylitol was 14.3% at pH 6.5, 8.9% at pH 7.5 and 7.4% at pH 8.5.

Figure 6C:
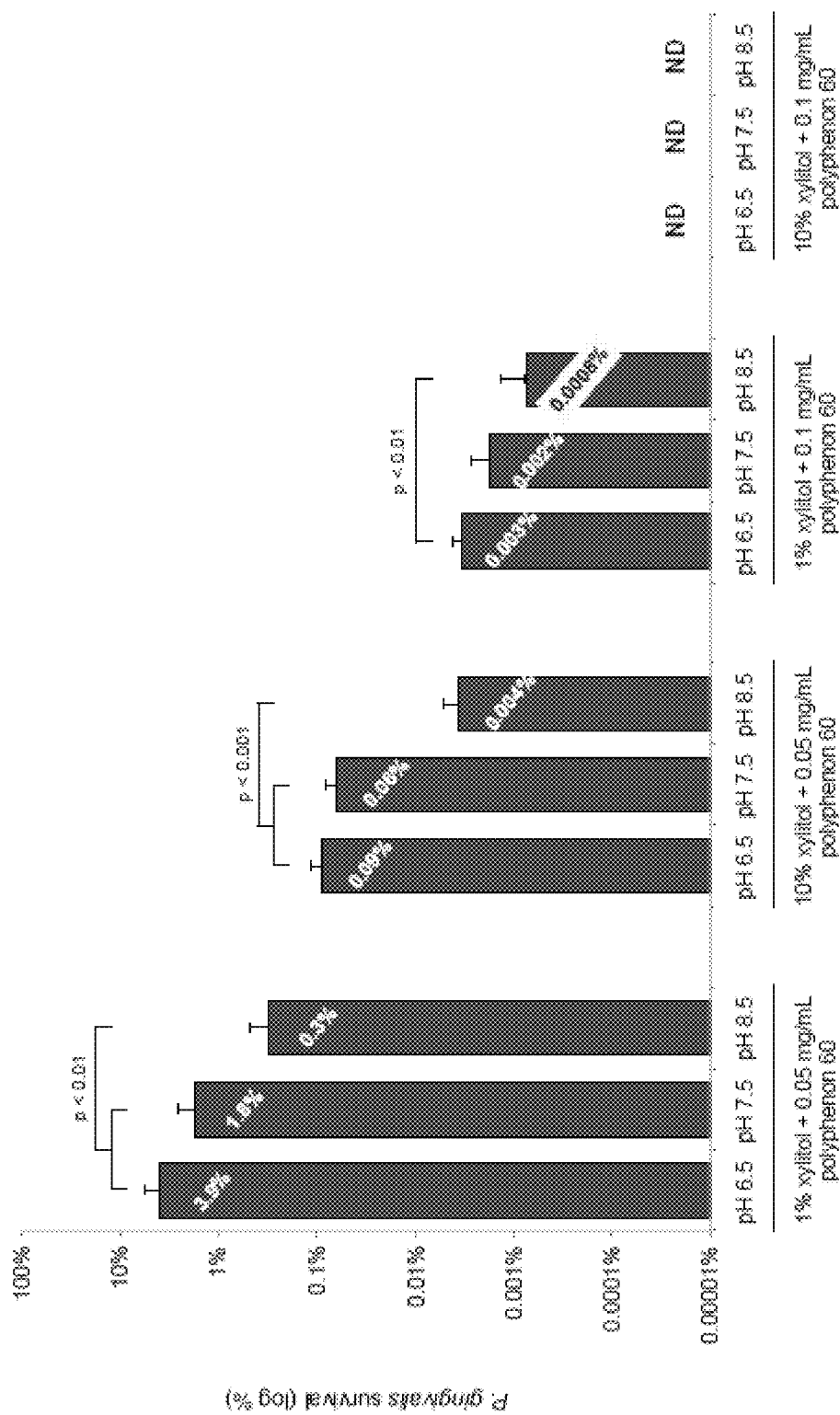

FIG. 6C shows the survival of *P. gingivalis* in the presence of a composition comprising xylitol and polyphenon 60 at differing pH. An upper limit of 0.1 mg/mL polyphenon 60 was used in order to be able to assess the pH effects. All combinations tested showed decreased survival of *P. gingivalis* compared to *P. gingivalis* survival in the presence of either xylitol or polyphenon 60 alone, at varying pH. For example, *P. gingivalis* survival in 0.05 mg/mL polyphenon 60 at pH 7.5 was 8.6%, in 1% xylitol was 63.2% at pH 7.5 and in a combination of 1% xylitol and 0.05 mg/mL polyphenon 60 was 1.8%. The combinations tested appeared to produce synergistic results.

Furthermore, *P. gingivalis* survival decreased with increasing pH. For example, *P. gingivalis* survival decreased from 3.9% in 1% xylitol and 0.05 mg/mL polyphenon 60 at pH 6.5, to 1.8% at pH 7.5 and to 0.3% at pH 8.5. Similarly, *P. gingivalis* survival decreased from 0.09% in 10% xylitol and 0.05 mg/mL polyphenon 60 at pH 6.5, to 0.06% at pH 7.5 to 0.04% at pH 8.5. *P. gingivalis* survival decreased from 0.003% in 1% xylitol and 0.1 mg/mL polyphenon 60 at pH 6.5, to 0.002% at pH 7.5 and to 0.0006% at pH 8.5. For 10% xylitol and 0.1 mg/mL polyphenon 60, all pH conditions kill *P. gingivalis* beyond detection.

Example 7: Inhibitory Effect of Tea Polyphenols and Erythritol on *Porphyromonas gingivalis* Growth at Differing pH

*P. gingivalis* ATCC 33277 was grown in the presence of erythritol and tea polyphenols (polyphenon 60) in acidic (pH 6.5±0.1), neutral (7.5±0.1) or alkaline (pH 8.5±0.1) pH. The percent inhibition was measured by normalizing the results against *P. gingivalis* grown in media with the corresponding pH adjustment.

Figure 7A:
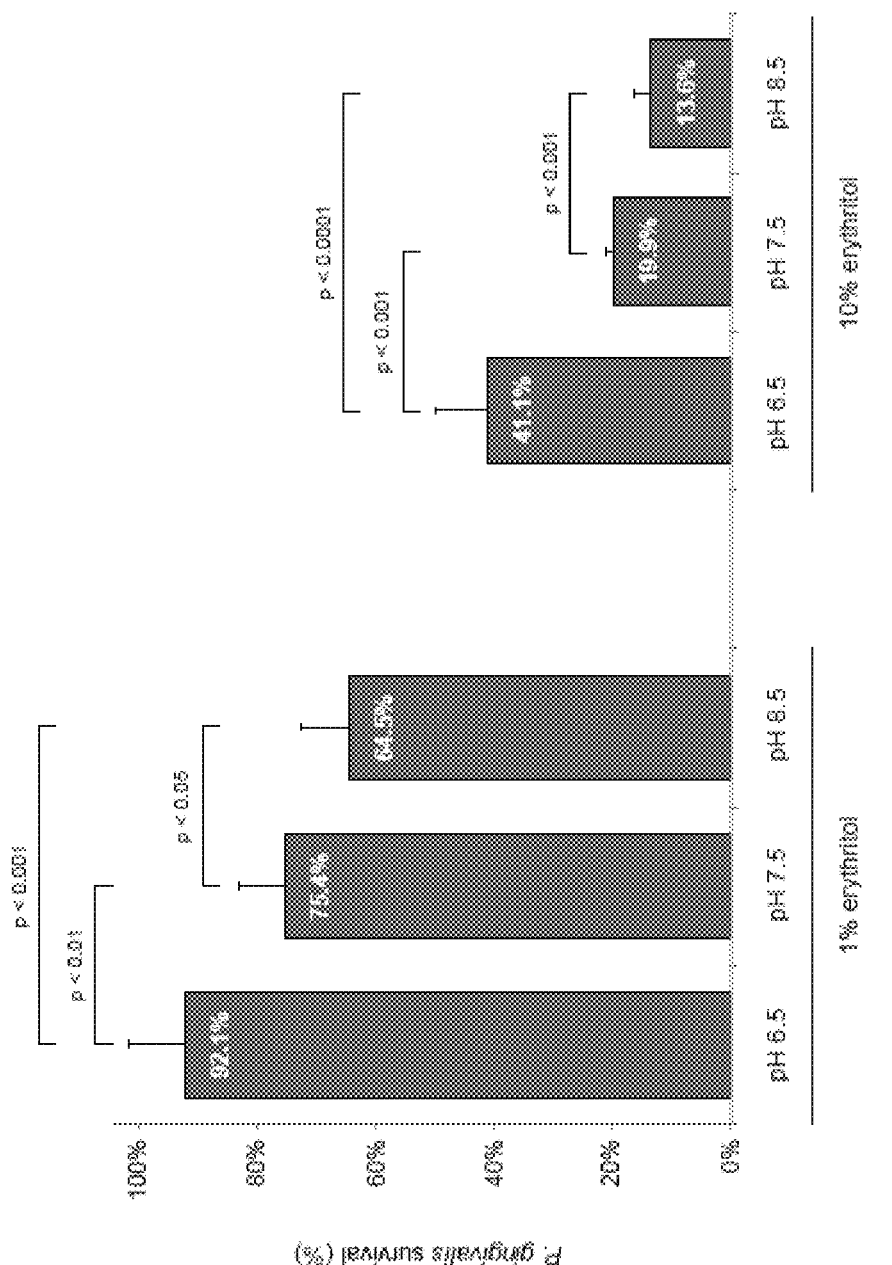
FIGS. 7A and 7B shows inhibitory effect of tea polyphenols and erythritol on *Porphyromonas gingivalis* growth at differing pH.

FIG. 7A shows the growth inhibition of erythritol with differing pH. A concentration of 10% erythritol showed decreased survival of *P. gingivalis* compared to a concentration of 1% erythritol at the same pH. For example, survival of *P. gingivalis* in 1% erythritol at pH 6.5 was 92.1% and in 10% erythritol at pH 6.5 was 41.1%. Survival of *P. gingivalis* also decreased with increasing pH. For example, survival of *P. gingivalis* in 10% erythritol was 41.1% at pH 6.5, 19.9% at pH 7.5 and 13.6% at pH 8.5. The effect of polyphenon 60 at differing pH and in the absence of a sugar alcohol is shown in FIG. 6A.

Figure 7B:
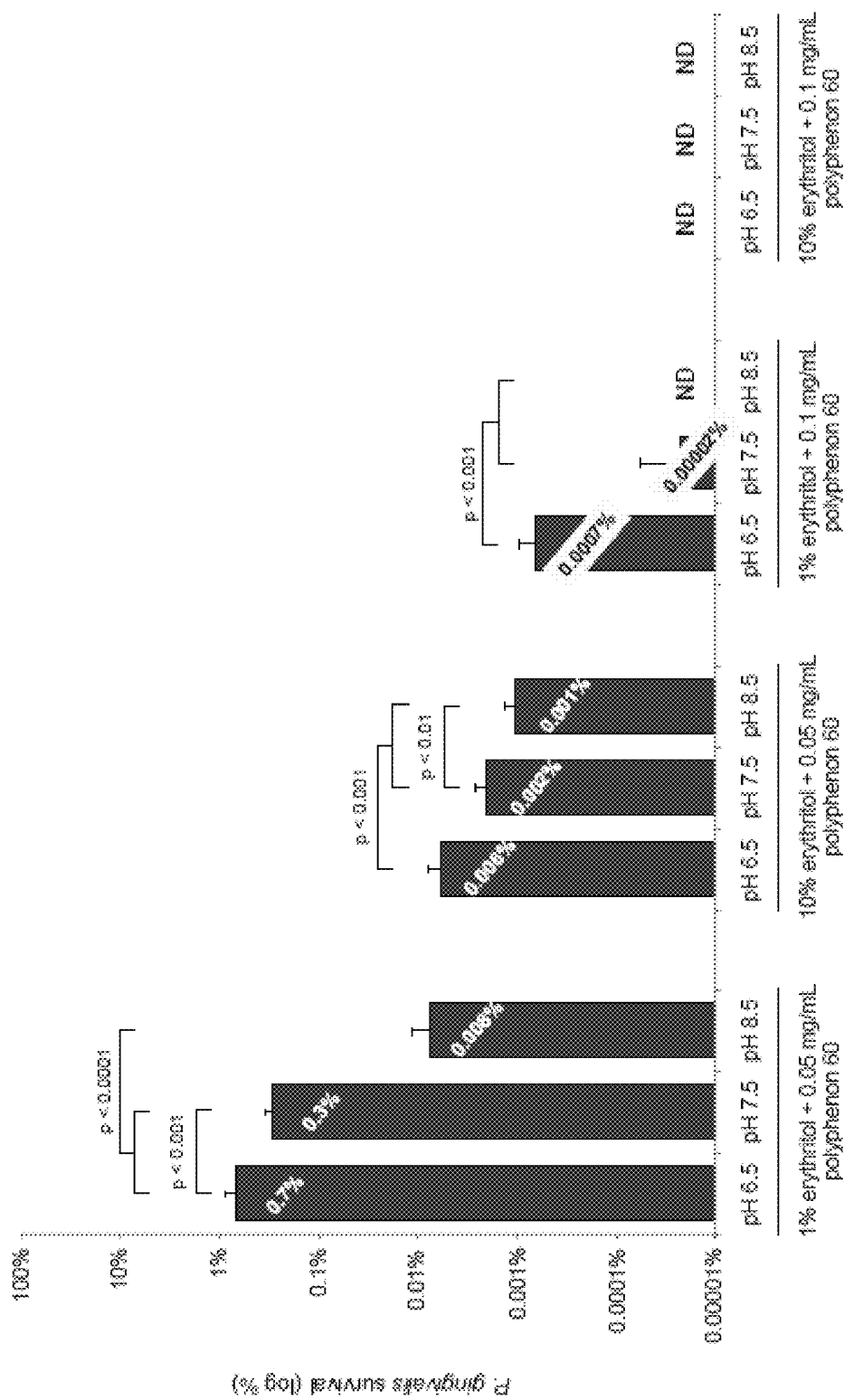

FIG. 7B shows the survival of *P. gingivalis* in the presence of a composition comprising both erythritol and polyphenon 60. An upper limit of 0.1 mg/mL polyphenon 60 was used in order to be able to assess pH effects. All combinations tested showed decreased survival of *P. gingivalis* and these decreases were greater compared to the effect shown by any of the components alone. For example, *P. gingivalis* survival in 0.05 mg/mL polyphenon 60 at pH 7.5 was 8.6%, in 1% erythritol was 75.4% at pH 7.5 and in a combination of 1% erythritol and 0.05 mg/mL polyphenon 60 was 0.3%. The combinations tested appeared to produce synergistic results.

Furthermore, *P. gingivalis* survival decreased with increasing pH. For example, *P. gingivalis* survival decreased from 0.7% in 1% erythritol and 0.05 mg/mL polyphenon 60 at pH 6.5, to 0.3% at pH 7.5 and to 0.08% at pH 8.5. Similarly, *P. gingivalis* survival decreased from 0.006% in 10% erythritol and 0.05 mg/mL polyphenon 60 at pH 6.5, to 0.002% at pH 7.5 to 0.001% at pH 8.5. *P. gingivalis* survival decreased from 0.0007% in 1% erythritol and 0.1 mg/mL polyphenon 60 at pH 6.5, to 0.00002% at pH 7.5. For 1% erythritol and 0.1 mg/mL polyphenon 60 at pH 8.5, *P. gingivalis* could not be detected. For 10% erythritol and 0.1 mg/mL polyphenon 60, all pH conditions kill *P. gingivalis* beyond detection.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

The invention claimed is:

1. A synergistically effective topical composition for topically inhibiting, reducing or preventing growth or biofilm formation of caries, gingivitis- and/or halitosis-causing bacteria in an oral cavity of a subject, the composition consisting of active agents and excipients, wherein the active agents consist of:
   0.005% (w/v) to 0.1% (w/v) of tea polyphenols produced by *Camellia sinensis* or corresponding polyphenols which are synthetically produced;
   a pH modulating agent for maintaining a pH of the composition between 7 and 8.5; and
   1% (w/v) to 10% (w/v) of a 3-carbon to a 24-carbon sugar alcohol,
   and the excipients consist of water, sodium alginate, glycerin and one or more than one flavouring agent,
   wherein the composition results in an inhibition of growth of at least 50%, or an inhibition of growth to a survival level of less than 5 log %, of gingivitis- and/or halitosis-causing bacteria as compared to growth of said bacteria in the presence of 0.005% (w/v) to 0.1% (w/v) of tea polyphenols alone,
   and wherein the composition is a drink.

2. The composition of claim 1, wherein the caries-, gingivitis- and/or halitosis-causing bacteria comprise *Streptococcus mutans, Streptococcus sobrinus, Lactobacillus species, Porphyromonas gingivalis, Tannerella forsythia, Treponema denticola, Fusobacterium nucleatum, Prevotella intermedia, Prevotella nigrescens, Aggregatibacter actinomycetemcomitans*, and/or *Solobacterium moorei*.

3. The composition of claim 1, wherein the caries-, gingivitis- and/or halitosis-causing bacteria comprise *Streptococcus mutans, Porphyromonas gingivalis* and/or *Solobacterium moorei*.

4. The composition of claim 1, wherein the tea polyphenols comprise (+)-catechin (C), (−)-epicatechin (EC), (−)-gallocatechin (GC), (−)-epicatechin gallate (ECG), (−)-epigallocatechin (EGC), (−)-epigallocatechin gallate (EGCG), Kaempferol, quercetin, myricetin, apigenin, luteolin, theaflavin-3-gallate, theaflvin-3-3-digallate or a combination thereof.

5. The composition of claim 1, wherein the sugar alcohol is arabitol, erythritol, glycerol, hydrogenated starch hydrolysates (HSH), isomalt, lactitol, maltitol, mannitol, sorbitol, xylitol or a combination thereof.

6. The composition of claim 1, wherein the sugar alcohol is xylitol or erythritol.

7. The composition of claim 1, wherein the pH modulating agent is a food-safe salt or a food-grade salt.

8. The composition of claim 1, wherein the pH modulating agent comprises sodium bicarbonate, potassium carbonate, calcium hydroxide, potassium hydroxide, potassium bicarbonate, sodium hydroxide or a combination thereof.

9. The composition of claim 1, wherein the composition consists of between 79% (v/v) and 99% (v/v) water.

10. A method of inhibiting, reducing or preventing growth or biofilm formation of caries-, gingivitis- and/or halitosis-causing bacteria in an oral cavity of a subject comprising topically contacting a composition as defined in claim 1 with the oral cavity of the subject.

11. The method of claim 10, wherein the composition is ingested by the subject.

12. The composition of claim 1, wherein the tea polyphenols produced by *Camellia sinensis* comprise a mixture of polyphenolic species comprising catechins.

13. The composition of claim 12, wherein the mixture of polyphenolic species further comprises any one or more of flaranols, flaraones, chlorogenic acid, phenolic acid, and glycosids.

* * * * *